(12) United States Patent
Ishii et al.

(10) Patent No.: US 8,547,424 B2
(45) Date of Patent: Oct. 1, 2013

(54) ENDOSCOPE SYSTEM AND LENS UNIT

(75) Inventors: Hiroshi Ishii, Tokyo (JP); Seiji Iwasaki, Hachioji (JP); Masahiro Kawauchi, Akiruno (JP); Hideaki Ishihara, Hachioji (JP); Susumu Takahashi, Iruma (JP); Shinichi Nakamura, Hino (JP); Azusa Noguchi, Hino (JP); Hideyasu Takato, Hino (JP); Tsutomu Sasamoto, Hino (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 1381 days.

(21) Appl. No.: 12/254,479

(22) Filed: Oct. 20, 2008

(65) Prior Publication Data

US 2009/0051764 A1    Feb. 26, 2009

Related U.S. Application Data

(63) Continuation of application No. PCT/JP2007/058354, filed on Apr. 17, 2007.

(30) Foreign Application Priority Data

Apr. 21, 2006    (JP) .................................. 2006-118240

(51) Int. Cl.
*A61B 1/06*    (2006.01)
*A61B 1/04*    (2006.01)

(52) U.S. Cl.
USPC ................ 348/68; 348/76; 600/181

(58) Field of Classification Search
USPC .................. 348/65–76; 600/101, 117–118, 600/181
See application file for complete search history.

(56) References Cited

U.S. PATENT DOCUMENTS

| 4,866,526 | A  | * | 9/1989 | Ams et al. ........................ 348/69 |
| 5,876,327 | A  |   | 3/1999 | Tsuyuki et al. |
| 5,966,168 | A  | * | 10/1999 | Miyazaki ......................... 348/68 |
| 7,892,169 | B2 | * | 2/2011 | Gono et al. ..................... 600/178 |
| 2003/0176768 | A1 | * | 9/2003 | Gono et al. .................... 600/109 |
| 2004/0143157 | A1 | * | 7/2004 | Doguchi et al. .............. 600/109 |
| 2007/0065135 | A1 | * | 3/2007 | Takei et al. .................... 396/241 |
| 2007/0098399 | A1 | * | 5/2007 | Yasunaga ...................... 396/508 |
| 2008/0062421 | A1 | * | 3/2008 | Zhou et al. .................... 356/418 |
| 2009/0156901 | A1 | * | 6/2009 | Gono ............................. 600/180 |

FOREIGN PATENT DOCUMENTS

| JP | 5-297285 | 11/1993 |
| JP | 07-264886 | 10/1995 |
| JP | 10-133126 | 5/1998 |
| JP | 10-151104 | 6/1998 |
| JP | 10-225427 | 8/1998 |
| JP | 2006-051334 | 2/2006 |

* cited by examiner

*Primary Examiner* — Patrice Winder
(74) *Attorney, Agent, or Firm* — Scully, Scott, Murphy & Presser, P.C.

(57) ABSTRACT

An endoscope system has a light source apparatus and an endoscope including an illumination optical system and an objective optical system. At least the objective optical system of the endoscope is provided with an adjustable diaphragm, and in a light path in one of the light source apparatus, the illumination optical system, and the objective optical system, an insertable/retractable filter for observation for special light is provided. The adjustable diaphragm performs a closing operation or an opening operation only when the filter for observation for special light is inserted into the light path.

8 Claims, 11 Drawing Sheets

ENDOSCOPE SYSTEM AND LENS UNIT

CROSS REFERENCE TO RELATED APPLICATION

This application is a continuation application of PCT/JP2007/058354 filed on Apr. 17, 2007 and claims benefit of Japanese Application No. 2006-118240 filed in Japan on Apr. 21, 2006, the entire contents of which are incorporated herein by this reference.

BACKGROUND OF INVENTION

1. Field of the Invention

The present invention relates to an endoscope system provided with a filter for observation for special light which is insertable/retractable into and out of a light path for illumination light or a light path for observation light.

2. Description of the Related Art

Conventionally, in observations for special light such as an NBI (Narrow Band Imaging) observation which is an observation using a narrow band light, an infrared light observation which is an observation using an infrared light, and a fluorescence observation which is an observation using fluorescence, there was a possibility that a subject image has a lower brightness as compared to that obtained in a normal white light observation. For example, Japanese Patent Application Laid-Open Publication No. 10-151104 discloses a fluorescence endoscope apparatus which uses a so-called adjustable diaphragm which changes the size of diaphragm between in a white light observation and an observation for special light so that the observations can be performed in one endoscope by switching a white light and a special light.

SUMMARY OF THE INVENTION

In order to achieve the above object, an endoscope system of the present invention including a light source apparatus and an endoscope having an illumination optical system and an objective optical system includes: an adjustable diaphragm which is provided at least in the objective optical system; and an insertable/retractable filter for observation for special light which is provided in a light path in one of the light source apparatus, the illumination optical system, and the objective optical system, wherein the adjustable diaphragm performs a closing operation or an opening operation only when the filter for observation for special light is inserted into the light path.

DETAILED DESCRIPTION OF THE PREFERRED EMBODIMENT(S)

Now, embodiments of the present invention will be explained below in detail with reference to the drawings.

In the following explanation, an image pickup unit of an insertion section of a videoscope has a front side toward a subject and a rear side toward an image pickup device.

Figure 1:
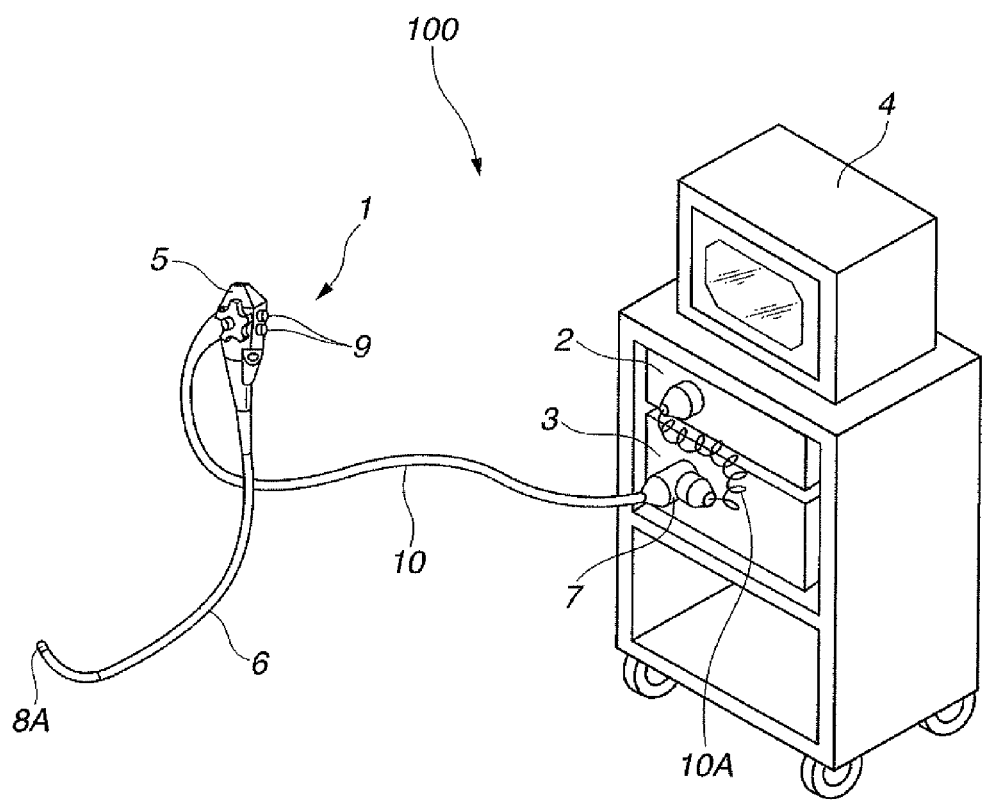
FIG. 1 is a view showing an entire configuration of a videoscope system according to a first embodiment of the present invention.
Figure 2:
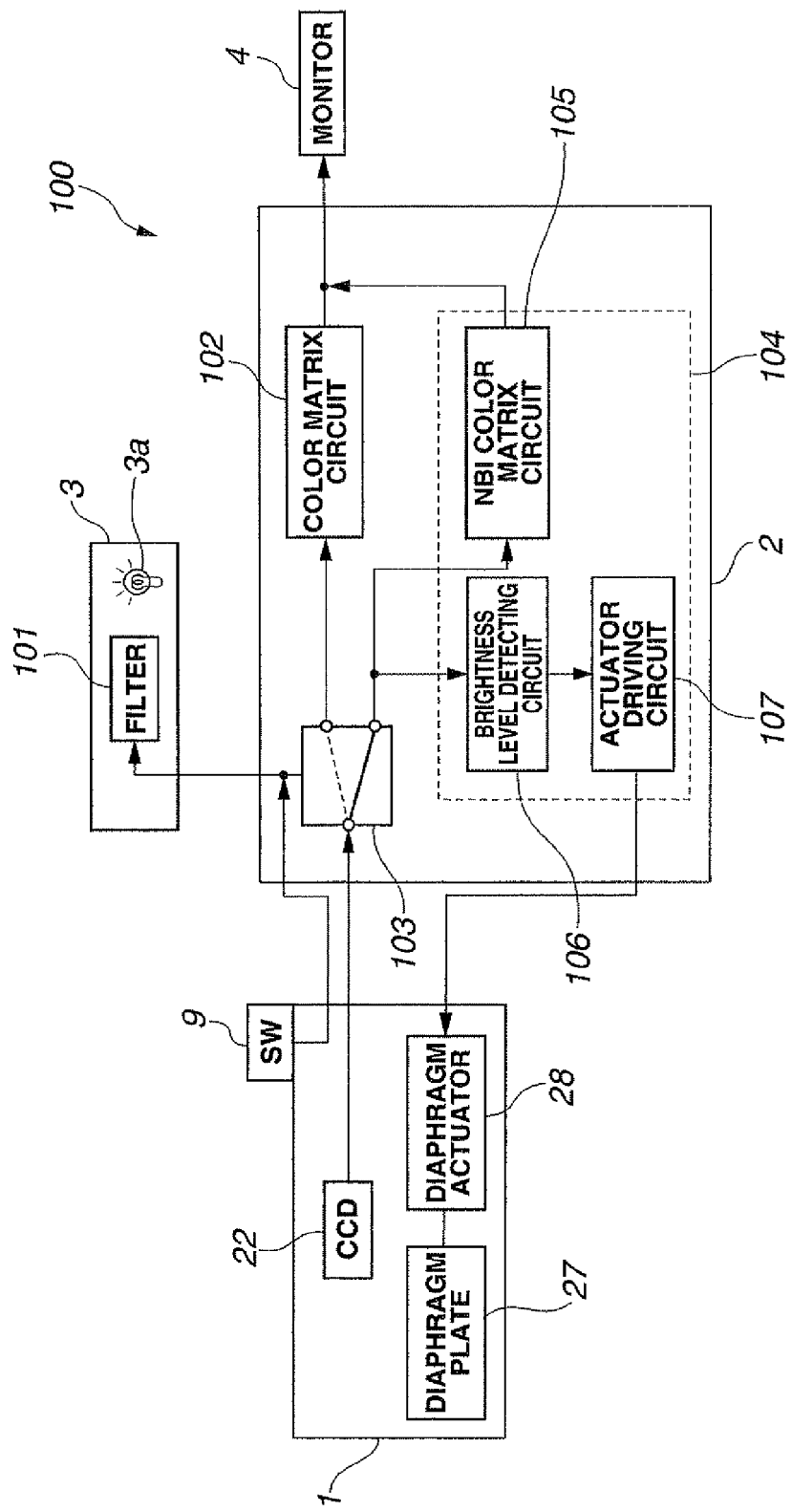
FIG. 2 is a block diagram illustrating a configuration of a control circuit which relates to a switching of observation modes in the videoscope system of FIG. 1.

A videoscope system 100 which is an endoscope system of the present embodiment is, as shown in FIGS. 1 and 2, mainly configured with a videoscope 1 which is an electronic endoscope, a light source apparatus 3 for supplying illumination light to the videoscope 1, a video processor 2 which receives image pickup signal from an image pickup unit 11 of the videoscope 1 (see FIG. 3) for image processing, and a monitor 4 for displaying an observation image of a subject based on image output signals from the video processor 2.

In the videoscope system 100, an operation of an operation switch 9 enables switching between an observation mode for normal light which uses a normal light and an observation mode for narrow band light which is an observation for special light (hereinafter, referred to as an NBI mode). In a normal light observation, an observation is performed by a normal light with an NBI filter 101 being retracted from the front portion (which is also referred to as a light path) of a light source 3a in the light source apparatus 3. In the normal light observation, as will be described later, an adjustable diaphragm unit 24 incorporated in the image pickup unit 11 (see FIG. 3) is remained in a stopped down state.

Meanwhile, in an observation for special light, an NBI observation is performed by irradiating a narrow band light to a subject with a filter for special light, for example the NBI filter 101, being inserted in the front portion of the light source 3a in the light source apparatus 3. In the NBI observation, the diaphragm of the adjustable diaphragm unit 24 is switched between an opened up state and a closed state depending on a brightness of the subject as will be described later.

In the configuration of the system according to the present invention, the switching of NBI modes between fluorescence observation mode and infrared light observation mode can be done by switching the above NBI filter to a filter for fluorescence observation or a filter for infrared light.

Now, the configuration of each control element of the videoscope system 100 will be explained below in detail.

The videoscope 1 includes an operation section 5, an insertion section 6, and a connector section 7.

The operation section 5 is provided with an operation switch 9 to switch between an observation mode for normal light and an NBI mode. The operation section 5 has a universal code 10 extended therefrom, the code 10 having the connector section 7 at the proximal end portion thereof. The universal code 10 includes a light guide and an electrical signal line inserted therethrough. The connector section 7 is connected to the light source apparatus 3. The connector section 7 and the video processor 2 are electrically connected to each other by an electrical cable 10A.

The insertion section 6 is connected to the operation section 5 at the proximal end thereof, and has a distal end portion 8A at the distal end thereof. The distal end portion 8A mainly has an image pickup unit 11 and an illumination optical system unit (not shown) incorporated therein.

The image pickup unit 11 is configured with a CCD 22 which is an image pickup device, an objective optical system which is a lens unit, and an adjustable diaphragm unit 24. The adjustable diaphragm unit 24 has, as shown in FIG. 6, a first substrate 25, a second substrate 26, a diaphragm plate 27 for an adjustable diaphragm, and a diaphragm actuator 28. The actuator 28 pivotally drives the diaphragm plate 27 between a stopped down position and an opened-up position. The image pickup unit 11 will be explained below in detail with reference to FIGS. 3 to 6.

The light source apparatus 3 has the white light source 3a such as xenon, and the light source 3a includes a light path in which a NBI filter 101 which transmits a light within a predetermined narrow band is arranged in an insertable/retractable manner. The filter 101 is driven to an inserted position in the light path of an illumination light or to a retracted position which is deviated from the light path in accordance with the signal of the operation switch 9 (SW of FIG. 2) of the operation section 5.

In the system in which a fluorescence or infrared light observation is performed as an observation for special light, a fluorescence filter or an infrared light filter is applied instead of the NBI filter 101 of the light source apparatus 3.

The video processor 2 has a video output switching circuit 103, a color matrix circuit 102, an NBI control circuit 104, and a control section (not shown) incorporated therein. The video output switching circuit 103 can be switched by a signal of the operation switch 9 of the operation section 5. The control section controls all of the video processor 2, the light source apparatus 3, and the videoscope 1.

The NBI control circuit 104 includes an NBI color matrix circuit 105, a brightness level detecting circuit 106, and an actuator driving circuit 107 which drives the diaphragm actuator 28.

In the videoscope system 100 having the above described configuration, when an observation mode for normal light is selected by the operation switch 9, the NBI filter 101 is retracted from the front portion of the light source 3a in the light source apparatus 3. Therefore, a normal light from the light source 3a is straightforwardly irradiated to a subject through the distal end portion 8A. In the observation mode for normal light, the video output switching circuit 103 is switched to the color matrix circuit 102 side as shown by the broken line, so that an output from the CCD 22 is inputted to the color matrix circuit 102. The image data output is processed by the color matrix circuit 102 to be outputted to the monitor 4, where an image by a normal light observation is displayed.

In the observation mode for normal light, an off signal is sent to the actuator driving circuit 107, 50 that the diaphragm actuator 28 is set to be in a non-energized state as will be described later, and the diaphragm plate 27 is controlled to be located at a stopped down position.

An operation of the operation switch 9 enables a switching of the observation mode from the observation mode for normal light to an NBI mode, That is, an operation of the operation switch 9 first causes the NBI filter 101 to be inserted to the front portion of the light source 3a in the light source apparatus 3. Thus, a normal light from the light source 3a passes the NBI filter 101, which causes only the narrow band light as the special light to transmit the illumination optical system unit of the distal end portion 8A to be irradiated to a subject.

Furthermore, an operation of the operation switch 9 causes the video output switching circuit 103 to be switched from the state shown by the broken line to the state shown by the solid line, so that an output from the CCD 22 is connected to the NBI color matrix circuit 105 and the NBI control circuit 104 side.

The output from the CCD 22 is signal-processed by the NBI color matrix circuit 105 in an appropriate manner for NBI, so that an image data by NBI is outputted to the monitor 4, where an image by the NBI observation is displayed. Simultaneously, the output from the CCD 22 is sent to the brightness level detecting circuit 106 of the NBI control circuit 104, where the brightness of the subject is measured. A switch of a depth is performed based on the measured brightness as a trigger.

In the observation mode for NBI, when the diaphragm plate 27 of the adjustable diaphragm unit 24 is moved to the stopped down position, a sufficient brightness cannot be obtained for a subject distance of 20 mm or more. Thus, when the brightness level detecting circuit 106 detects a brightness of a subject which is equal to or less than a certain level in a middle to long distance observation, an on signal is sent from the brightness level detecting circuit 106 to the actuator driving circuit 107 to cause the diaphragm plate 27 of the adjustable diaphragm unit 24 to be opened up. Then, the actuator driving circuit 107 causes the diaphragm actuator 28 to be in an energized state, as will be described below, to control the diaphragm plate 27 to be pivotally driven to an opened-up position.

To the contrary, in a short distance observation with the diaphragm being opened up, the brightness level detecting circuit 106 detects a brightness which is equal to or more than a certain level. Then, an off signal is sent from the brightness level detecting circuit 106 to the actuator driving circuit 107 to close the diaphragm plate 27, as the result of that the actuator driving circuit 107 causes the diaphragm actuator 28 to be in a non-energized state, as will be described below, to control the diaphragm plate 27 to be pivotally driven to a stopped down position.

In the normal light observation, as will be described later, the diaphragm actuator 28 does not have to be energized. However, in the NBI observation, the NBI filter 101 is switched to be inserted in the light path of the illumination light in the light source apparatus 3, so that only in a middle to long distance observation, as described above, an observation can be performed as in the normal light observation by moving the diaphragm plate 27 to an opened-up position. Therefore, even if the video processor 2 and the light source apparatus 3 are not the systems which are adapted to an NBI observation, only for a normal light observation, the videoscope 1 can be used as it is like the conventional type apparatus. Also, an NBI observation with sufficient brightness and depth can be performed by using the same illumination light as that in the normal light observation, for example a scope having the same outer diameter.

Now, the configuration of the distal end portion 8A of the videoscope 1 having the image pickup unit 11 incorporated therein will be explained below in detail with reference to FIGS. 3 to 6.

Figure 3:
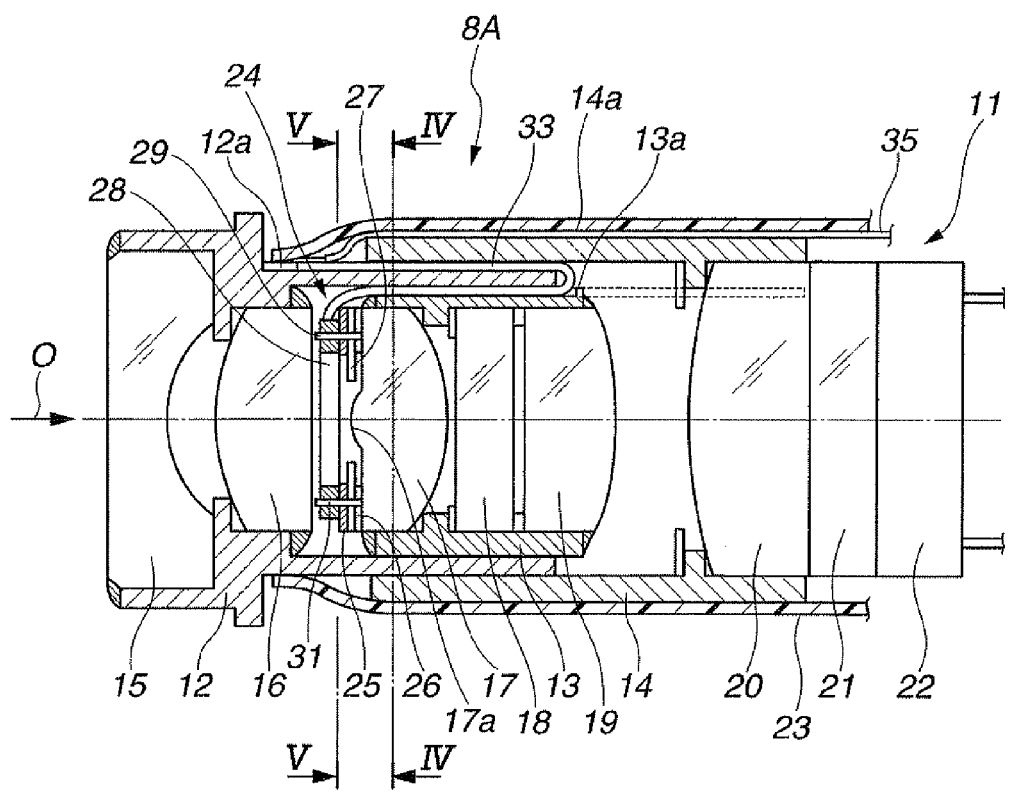
FIG. 3 is a cross sectional view showing a distal end portion, especially portions around an image pickup unit, of the videoscope system of FIG. 1.

In the videoscope 1, the distal end portion 8A of the insertion section 6 which is to be inserted into a body cavity has the image pickup unit 11 incorporated therein as shown in FIG. 3.

The image pickup unit 11 is an image pickup optical system which is disposed along an optical axis O. The image pickup unit 11 includes a first lens frame 12, a second lens frame 13, and a third lens frame 14. The first lens frame 12 is disposed on a subject side.

The first lens frame 12 has a first lens 15 and a second lens 16 fixed thereto, by adhesion for example. The second lens frame 13 is held at an inner periphery of a rear portion of the first lens frame 12. The second lens frame 13 has a third lens 17, a fourth lens 18, and a fifth lens 19 fixed thereto, by adhesion for example. The third lens 17 has an adjustable diaphragm unit 24 fixed to the front portion thereof, by adhesion for example. The third lens frame 14 has a lens for centering 20 fitted into the inner periphery of a rear portion thereof, and the lens for centering 20 is fixed to the inner periphery by adhesion for example. The lens for centering 20 has the CCD 22 adhesively fixed thereto via a CCD cover glass 21.

The third lens 17 is a bifocal lens. The third lens 17 has a convex portion 17a which is disposed on a plane surface side of the plano-convex lens and has a diameter smaller than the outer diameter of the plane surface, that is the same diameter as the inner diameter of the diaphragm when closed by the adjustable diaphragm unit 24, and has a large curvature. Relative to the convex portion 17a, the adjustable diaphragm unit 24 is arranged so as to be centered with respect to the convex portion 17a.

The lens for centering 20 is centered with an image area (not shown) and is adhesively fixed to the CCD cover glass 21 of the CCD 22.

The third lens frame 14 is held at the outer periphery of the rear portion of the first lens frame 12 having the same focus with the first lens frame 12 and the second lens frame 13 which is fixedly fitted in the first lens frame 12.

The adjustable diaphragm unit 24 is configured with a first substrate 25 and a second substrate 26 which are metallic plate members as shown in FIG. 6, the diaphragm plate 27 which is an adjustable diaphragm, and the diaphragm actuator 28. The diaphragm actuator 28 is an ion conductive actuator connected to the FPC connector 33 which is a strip one-side flexible substrate as power supplying means.

The first substrate 25 and the second substrate 26 have diaphragm open apertures 25a and 26a which have an identical diameter and are centrally formed therein, respectively, The diaphragm open apertures 25a and 26a provide an aperture when the diaphragm is in an opened up state. The first substrate 25 and the second substrate 26 are also provided with a pivotally supporting pin 30 for pivotally supporting the diaphragm plate 27. The first substrate 25 and the second substrate 26 are further provided with a movement groove 25b through which a moving pin 31 is movably inserted. Another movement groove provided in the second substrate 26 is not shown in FIG. 6.

The diaphragm plate 27 includes a diaphragm opening 27a having a diaphragm diameter of a diaphragm in a stopped down state which provides a large depth of field, in other words a large focal depth. The diaphragm plate 27 is pivotally support by the pivotally supporting pin 30 between the first substrate 25 and the second substrate 26.

The diaphragm actuator 28 has an arc section. The diaphragm actuator 28 has one end which is supported onto the first substrate 25 by an actuator locking pin 29 formed of an insulation member, and the other end which has the moving pin 31 attached thereto. The moving pin 31 is slidably inserted into the movement groove 25b of the first substrate 25 to be fitted in the diaphragm plate 27.

The one end of the diaphragm actuator 28 is connected with a lead electrode 34 of the FPC connector 33 which is disposed on the insulation plate 32, at the inner surface and the outer surface on the one end. When the actuator driving circuit 107 energizes the diaphragm actuator 28 via the FPC connector 33 to cause a potential difference between the inner side and the outer side of the arc section, the diaphragm actuator 28 is deformed starting from the locking pin 29, resulting in a change of the curvature thereof.

Figure 5:
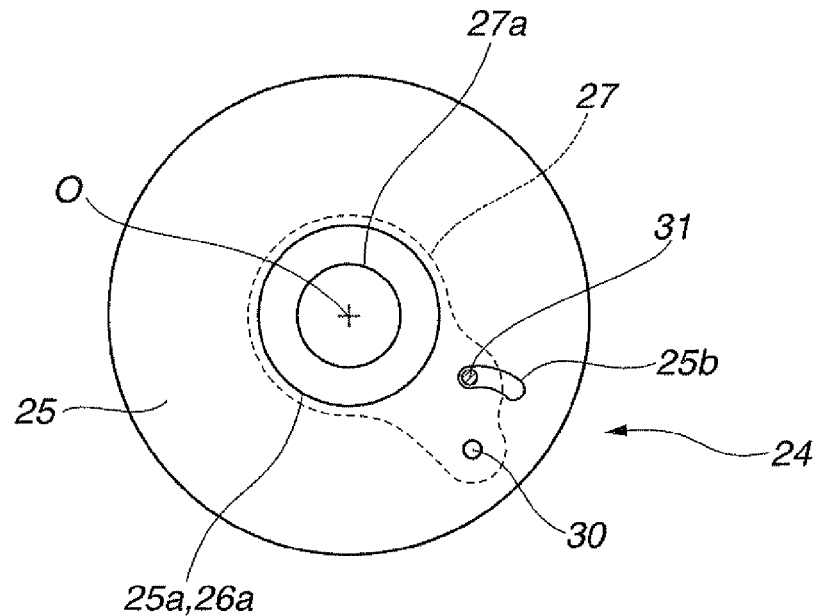
FIG. 5 is a cross sectional view taken along the line V-V of FIG. 3.
Figure 6:
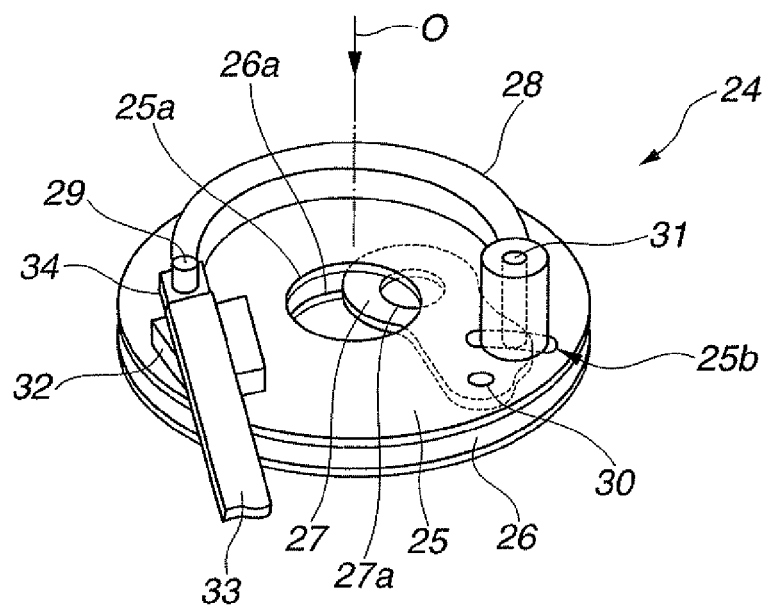
FIG. 6 is a perspective view showing an adjustable diaphragm unit incorporated in the image pickup unit of FIG. 3, which is seen from a subject side.

As the curvature of the diaphragm actuator 28 is changed, the moving pin 31 moves along the movement groove 25b, and the diaphragm plate 27 is pivotally driven, which causes the diaphragm plate 27 to move to an opened-up position where the diaphragm plate 27 is completely retracted from the diaphragm open aperture 25a of the first substrate 25 and the diaphragm open aperture 26a of the second substrate 26, and to a stopped down position where the diaphragm opening 27a of the diaphragm plate 27 shown in FIG. 5 is concentrically aligned with the diaphragm open apertures 25a and 26a.

That is, when the diaphragm plate 27 is at an opened-up position, the diaphragm of the image pickup optical system is provided by the diaphragm open apertures 25a and 26a, and when the diaphragm plate 27 is at a stopped down position, the diaphragm of the image pickup optical system is provided by the diaphragm opening 27a.

The above described curvature of the diaphragm actuator 28 is set to be increased in a non-energized state to cause the diaphragm plate 27 to be located to the above described stopped down position. While, the above described curvature of the diaphragm actuator 28 is set to be decreased in an energized state to cause the diaphragm plate 27 to be retracted to the above described diaphragm opened-up position.

The insertion and connection of the above described FPC connector 33 and the actuator driving cable 35 as power supplying means to each of the lens frames will be explained below.

Figure 4:
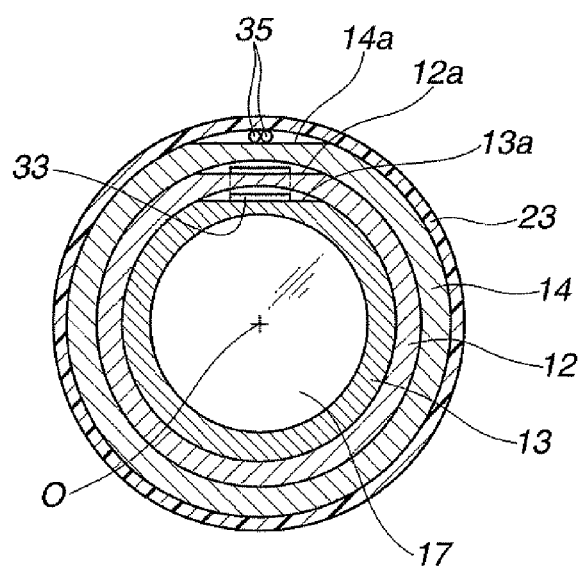
FIG. 4 is a cross sectional view taken along the line IV-IV of FIG. 3.

The FPC connector 33 is inserted through an outer peripheral D-shaped cut portion 13a of the second lens frame 13 as shown in FIGS. 3 and 4, and is bended into a U-shape, so that the FPC connector 33 is inserted through an outer peripheral D-shaped cut portion 12a of the first lens frame 12 to be guided out of the first lens frame 12. The guided FPC connector 33 has a connecting terminal portion to which a 2-wire actuator driving cable 35 is connected by soldering. The actuator driving cable 35 is inserted through an outer peripheral D-shaped cut portion 14a of the third lens frame 14 to be guided to the proximal end side of the distal end portion 8A. The actuator driving cable 35 has a thickness which does not exceed the outer peripheral D-shaped cut portion 14a of the third lens frame 14.

The outer peripheral D-shaped cut portion 13a of the second lens frame 13, the outer peripheral D-shaped cut portion 12a of the first lens frame 12, and the outer peripheral D-shaped cut portion 14a of the third lens frame 14 are provided along the axial direction, respectively. The second lens frame 13, the first lens frame 12, and the third lens frame 14 are inserted with the phases of each of the outer peripheral D-shaped cut portions 13a, 12a, and 14a are aligned, and are adhesively fixed to each other.

The connected FPC connector 33, the actuator driving cable 35, and the connection between the FPC connector 33 and the actuator driving cable 35 are sealed by an adhesive. That is, an adhesive is filled in the gap between the outer peripheral D-shaped cut portion 13a to which the FPC connector 33 is disposed and the inner periphery of the first lens frame 12 and the gap between the outer peripheral D-shaped cut portion 12a and the inner periphery of the third lens frame 14 for sealing, and an adhesive is used at a concave portion of the outer peripheral D-shaped cut portion 14a of the third lens frame 14 to which the actuator driving cable 35 is disposed and the connection between the FPC connector 33 and the actuator driving cable 35 for sealing. The third lens frame 14 is covered with a heat shrinkable tube 23 at the outer periphery thereof, so as to make the connection and the portion around the adjustable diaphragm unit 24 sealed in a watertight manner.

Operations in a normal light observation and an NBI operation in the videoscope system 100 having the above described configuration will be individually explained below with reference to FIGS. 7A to 7C.

When the operation switch 9 is operated to select an observation mode for normal light, as described above, the NBI filter 101 is moved to the retracted position in the light source apparatus 3, and a white light is irradiated to a subject. Also, the video output switching circuit 103 is switched to the color matrix circuit 102 side shown by the broken line, so that an image pickup output of the CCD 22 is processed at the color matrix circuit 102 and an image data in a normal light observation is displayed on the monitor 4.

Since the diaphragm actuator 28 is not energized, the diaphragm plate 27 is at the stopped down position shown in FIG. 5. At this point of time, the diaphragm is provided by the diaphragm opening 27a. In the normal light observation state, the depth of field which corresponds to the focal depth as shown in FIG. 7A ranges from the 100 mm far point of a subject distance to the 5 mm near point of the subject distance (which is equal to a routine scope). In the normal light observation state, a sufficient brightness is obtained because the NBI filter 101 is not inserted, thereby the range from the far point to the near point provides the observable brightness range. That is, in a normal light observation state, the range from the far point to the near point is observable.

Meanwhile, when the operation switch 9 is operated to select an NBI mode, as described above, the NBI filter 110 is moved to the inserted position in the front surface of the light source 3a in the light source apparatus 3, and a narrow band light is irradiated to a subject. Also, the video output switching circuit 103 is switched to the NBI color matrix circuit 105 and the NBI control circuit 104 side as shown by the solid line.

Therefore, an image pickup output from the CCD 22 is processed at the NBI color matrix circuit 105 and an image data in NBI is displayed on the monitor 4. Simultaneously, the brightness of the subject is measured by the brightness level detecting circuit 106 using the output from the CCD 22, so that the diaphragm actuator 28 is drive controlled depending on the brightness based on the measured result, which causes the diaphragm plate 27 to be switched to move to the stopped down position shown in FIG. 5 or retract from the diaphragm open apertures 25a and 26a to the opened-up position.

In a near point observation, that is, when a sufficient brightness is obtained with the subject distance from the 5 mm near point at to a 20 mm point (which is also referred to as a middle point), the actuator driving circuit 107 does not energize the diaphragm actuator 28. As a result, the diaphragm plate 27 remains at the stopped down position shown in FIG. 5. In this case, the depth of field corresponds to, as shown in FIG. 7B, the range from the 100 mm far point to the 5 mm near point of the subject distance, but the distance to the observed subject is equal to the range from the near point to the middle point, which is secured as an observable depth.

However, in a far point observation, specifically in a middle to far point observation, that is, for a subject distance from 20 mm to the 100 mm far point, a sufficient brightness cannot be obtained. In this case, the actuator driving circuit 107 energizes the diaphragm actuator 28.

As a result, the diaphragm plate 27 is caused to move to the opened-up position where the diaphragm plate 27 is retracted from the diaphragm open apertures 25a and 26a, so that the diaphragm is provided by the diaphragm open apertures 25a and 26a of the substrates 25 and 26. In this state, the diaphragm plate 27 is moved to the opened-up position, thereby, as shown in FIG. 7C, the depth of field ranges from the 20 mm middle point to the 100 mm far point of the subject distance, while the observable brightness can be obtained within the range from the 100 mm far point to the 5 mm near point of the subject distance.

Therefore, the range of the depth of field which is provided by the subject distance from the 20 mm middle point to the 100 mm far point can be secured as an observable depth.

As described above, in the videoscope system 100 of the present embodiment, in a near point observation with the NBI filter 101 being inserted in a light path in an NBI mode, the adjustable diaphragm unit 24 is closed, and in a middle to far point observation, the adjustable diaphragm is opened up. Therefore, unlike the above described conventional example in which the insertion section 6 having a light guide inserted therein for an observation for special light has an increased diameter, even in an observation for special light, an observable depth and brightness can be obtained as in the case of a normal light observation using a white light Thus, a small size like that of an objective optical system having a fixed focus without an adjustable diaphragm can be achieved.

Moreover, the configuration of the distal end portion 8A of the videoscope 1, as described above, has a good assembility, is easy to be watertight, has a good moisture resistance, and enables a check of diaphragm operation during its assembly or in a assembled unit state. The configuration has less failure due to dust, or possibility of generation of flare, and secures the accuracy and strength of lens frames, thereby various effects can be obtained including a good optical property.

In the videoscope system 100 of the present embodiment, a normal light observation can be performed even when a video processor which is not adapted to an observation for special light is used.

Next, a videoscope system of a second embodiment of the present invention will be explained below with reference to FIGS. 8 to 13.

A videoscope system of the present embodiment is similar to the videoscope system 100 of the first embodiment shown in FIG. 1 except the configurations of a light source apparatus, a video processor, and an image pickup unit incorporated in a videoscope. That is, in the videoscope system of the present embodiment, a light source apparatus does not include the NBI filter 101 which is a filter for special light. The actuator driving circuit 107 of the video processor 2 for driving a diaphragm has a filter actuator driving circuit (not shown) incorporated therein for driving a filter 50 incorporated in an image pickup unit 41 which is drive controlled by output of the operation switch 9.

The image pickup unit 41 disposed at the distal end portion 8B of the videoscope of the present embodiment includes a filter/adjustable diaphragm unit 49 incorporated therein, instead of the adjustable diaphragm unit 24.

Figure 8:
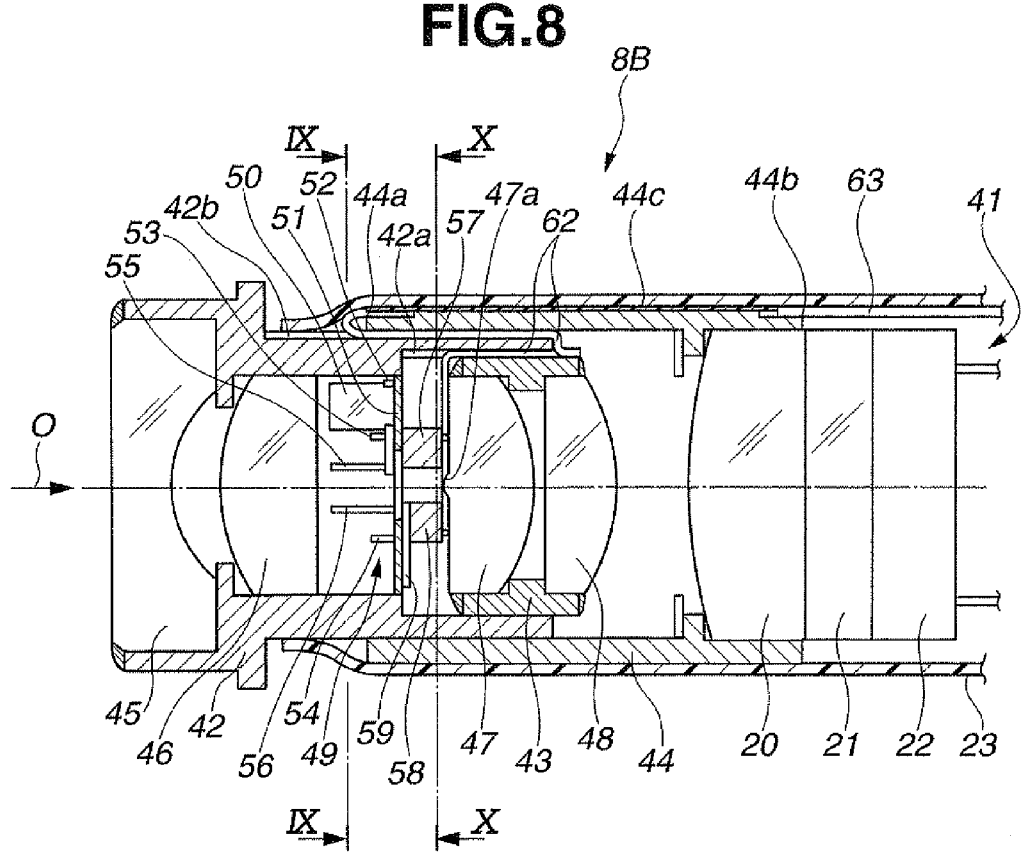
FIG. 8 is a cross sectional view showing a distal end portion, especially portions around an image pickup unit of a videoscope insertion section which is applied to a videoscope system according to a second embodiment of the present invention.

Specifically, the image pickup unit 41 is, as shown in FIG. 8, an image pickup optical system which is disposed along an optical axis O, and includes a first lens frame 42, a second lens frame 43, and a third lens frame 44. The first lens frame 12 is disposed on a subject side.

The first lens frame 42 has a first lens 45 and a second lens 46 fixed thereto by adhesion. The second lens frame 43 is held at an inner periphery of a rear portion of the first lens frame 42. The second lens frame 43 has a third lens 47 and a fourth lens 48 fixed thereto by adhesion. The third lens frame 44 has a lens for centering 20 fitted to the inner periphery of a rear portion thereof, and the lens for centering 20 is fixed to the inner periphery by adhesion. Between the second lens 46 in the first lens frame 42 and the third lens 47 in the second lens frame 43, a filter/adjustable diaphragm unit 49 is provided. The lens for centering 20 has the CCD 22 adhesively fixed thereto via a CCD cover glass 21.

The third lens 47 is a bifocal lens. The third lens 47 has a convex portion 47a which is disposed on a plane surface side of the plano-convex lens and has a diameter smaller than the outer diameter of the plane surface, and has a large curvature. The filter/adjustable diaphragm unit 49 is arranged so as to be centered with respect to the convex portion 47a.

The lens for centering 20 is centered with an image area (not shown) and is adhesively fixed to the CCD cover glass 21 of the CCD 22.

The third lens frame 44 is held at the outer periphery of the rear portion of the first lens frame 42 in having the same focus with the first lens frame 42 and the second lens frame 43 which is fixedly fitted in the first lens frame 42.

Figure 9:
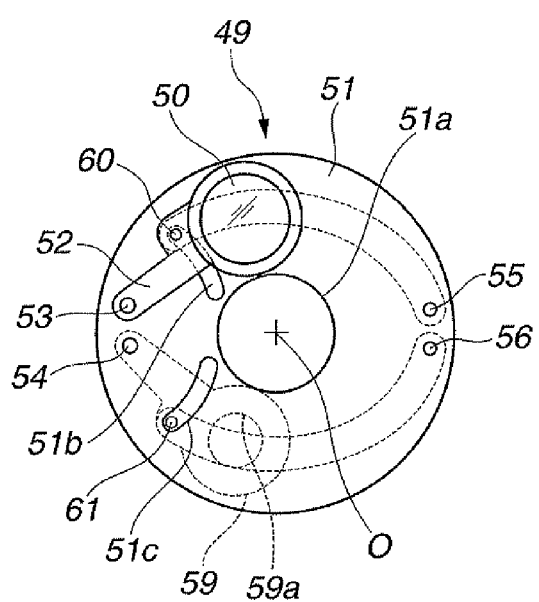
FIG. 9 is a cross sectional view taken along the line IX-IX of FIG. 8.
Figure 10:
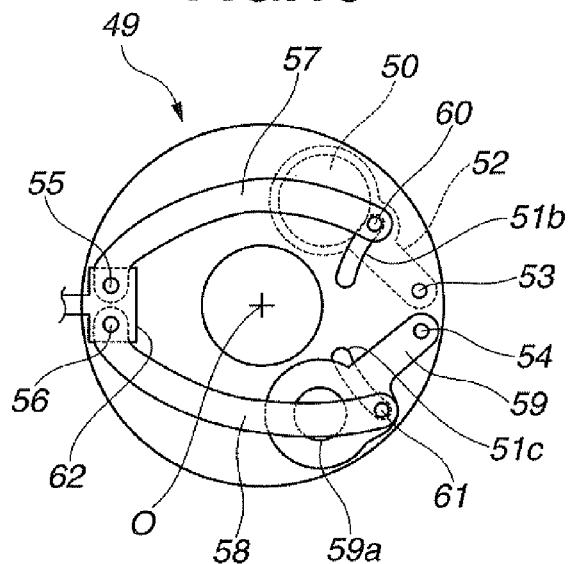
FIG. 10 is a cross sectional view taken along the line X-X of FIG. 8.

The filter/adjustable diaphragm unit 49 is configured with, as shown in FIGS. 8 to 10, a substrate 51 which is a metallic member, a filter supporting plate 52, a diaphragm plate 59 which is a filter adjustable diaphragm, a filter actuator 57, and a diaphragm actuator 58. The filter supporting plate 52 holds an NBI filter 50 for example which is a filter for special light. The filter actuator 57 is a first actuator, and the diaphragm actuator 58 is a second actuator. The actuators 57 and 58 are ion conductive actuators connected to an FPC connector 62 which is a strip one-side flexible substrate as power supplying means.

The substrate 51 is fixedly attached to an inner periphery of a rear portion of the first lens frame 42. The substrate 51 has a diaphragm open aperture 51a centrally formed therein which provides an opening with the diaphragm being in an opened up state. The substrate 51 is also provided with a pivotally supporting pin 53 for pivotally supporting the filter supporting plate 52, a pivotally supporting pin 54 for pivotally supporting the diaphragm plate 59, an actuator locking pin 55 for holding the filter actuator 57, and an actuator locking pin 56 for holding the diaphragm actuator 58. The substrate 51 is further provided with a movement groove 51b through which an actuator moving pin 60 is movably inserted, and a movement groove 51c through which an actuator moving pin 61 is movably inserted.

The filter supporting plate 52 has a front surface on which the NBI filter 50 is held. The filter supporting plate 52 holding the NBI filter 50 is pivotally supported by a pivotally supporting pin 53 onto the front surface of the substrate 51. Thus, the filter supporting plate 52 is pivotally driven by the moving pin 60 on the filter actuator 57 side between an inserted position and a retracted position which will be explained later.

The diaphragm plate 59 has a diaphragm opening 59a formed therein, the diaphragm opening 59a having a diaphragm diameter for providing a diaphragm in a stopped down state which achieves the largest depth at a diffraction limit. The diaphragm plate 59 is pivotally supported by a pivotally supporting pin 54 onto the rear surface of the substrate 51. Thus, the diaphragm plate 59 is pivotally driven by the moving pin 61 on the diaphragm actuator 58 side between an opened-up position and a stopped down position which will be explained later.

The filter actuator 57 includes an arc section, and has one end which is supported onto the rear surface of the substrate 51 by an actuator locking pin 55 formed of an insulation member and the other end which has the moving pin 60 attached thereto. The moving pin 60 is slidably inserted into the movement groove 51b of the substrate 51 to be fitted in the filter supporting plate 52.

Meanwhile, the diaphragm actuator 58 includes an arc section, and has one end which is supported onto the rear surface of the substrate 51 by an actuator locking pin 56 formed of an insulation member and the other end which has the moving pin 61 attached thereto. The moving pin 61 is slidably inserted into the movement groove 51c of the substrate 51 to be fitted in the diaphragm plate 59.

The diaphragm actuator 58 is configured to have a thickness which is smaller than that of the filter actuator 57 by the thickness of the diaphragm plate 59.

Figure 11:
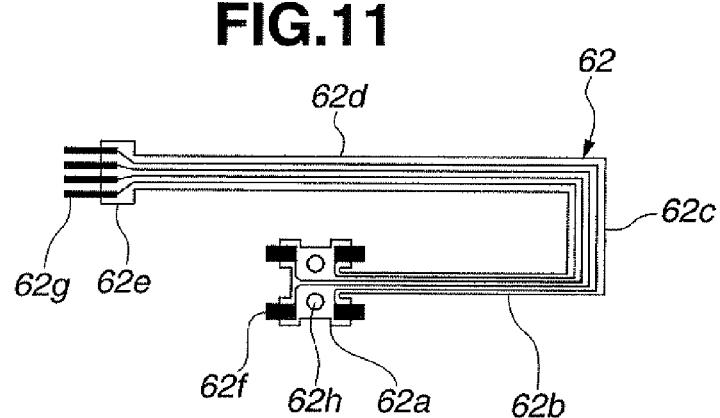
FIG. 11 is a development showing an FPC connector which forms a filter/adjustable diaphragm unit of FIG. 10.
Figure 13:
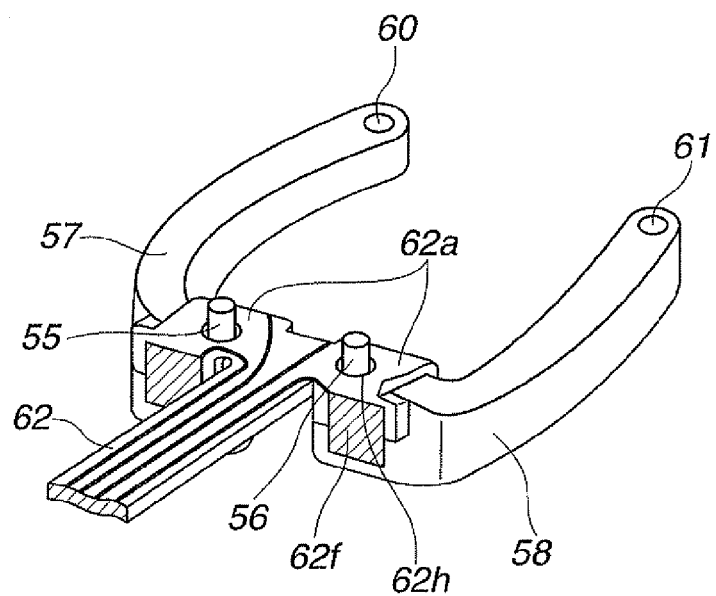
FIG. 13 is a perspective view showing the outline of an actuator which is applied to the filter/adjustable diaphragm unit of FIG. 10.

The filter actuator 57 and the electrode surfaces on the inner and outer sides of the one end of the diaphragm actuator 58 are connected with four lead electrodes 62f which are provided to the actuator connecting terminal portion 62a at one end of the FPC connector 62 shown in FIG. 11. As a specific example, the FPC connector 62 and the filter actuator 57, and the FPC connector 62 and the diaphragm actuator 58 are connected as shown in FIG. 13. The FPC connector 62 includes a bended portion 62c as shown in FIG. 11, and extended portions 62b and 62d which are configured to extend side by side in the same direction from the ends of the bended portion 62c.

When the actuator driving circuit 107 having the filter actuator driving circuit energizes the filter actuator 57 via the FPC connector 62 to cause a potential difference between the inner side and the outer side of the arc section, the filter actuator 57 is deformed starting from the locking pin 55, resulting in a change of the curvature thereof. When the actuator driving circuit 107 energizes the diaphragm actuator 58 via the FPC connector 62 to cause a potential difference between the inner side and the outer side of the arc section, the diaphragm actuator 58 is deformed starting from the locking pin 56, resulting in a change of the curvature thereof.

As the curvature of the filter actuator 57 is changed, the moving pin 60 moves, and the filter supporting plate 52 is pivotally driven, which causes the filter supporting plate 52 to move to an inserted position where the filter 50 is positioned on the diaphragm open aperture 51a of the substrate 51, and to a retracted position where the filter 50 is retracted from the aperture 51a. Similarly, as the curvature of the diaphragm actuator 58 is changed, the moving pin 61 moves, and the diaphragm plate 27 is pivotally driven, which causes the diaphragm plate 59 to move to a stopped down position where the diaphragm opening 59a is positioned centrally of the diaphragm open aperture 51a of the substrate 51 and an opened-up position where the diaphragm plate 59 is retracted from the aperture 51a.

The above described curvature of the filter actuator 57 is set to be increased in an energized state to cause the filter 50 to be located to the above described inserted position, and also is set to be decreased in a non-energized state to cause the filter 50 to be retracted to the above described retracted position. While, the above described curvature of the diaphragm actuator 58 is set to be increased in a non-energized state to cause the diaphragm plate 59 to be located to the above described stopped down position, and also is set to be decreased in an energized state to cause the diaphragm plate 59 to be retracted to the above described diaphragm opened-up position.

The insertion and connection of the above described FPC connector 62 and the actuator driving cable 63 as power supplying means to each of the lens frames will be explained below.

Figure 12:
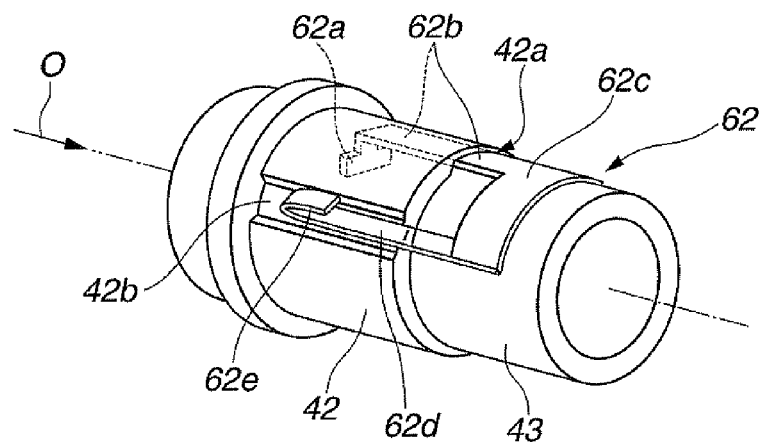
FIG. 12 is a perspective view showing a lens frame in a pulled-out state which forms the image pickup unit of the FPC connector of FIG. 11.

The FPC connector 62 is provided with a connecting terminal portion 62e having a lead electrode portion 62g at the other end thereof, with respect to the actuator connecting terminal portion 62a at one end thereof shown in FIG. 11. As shown in FIG. 12, the bended portion 62c of the FPC connector 62 is disposed on the outer surface of the second lens frame 43, and the extended portion 62b is inserted into an inner peripheral groove 42a of the first lens frame 42 which is formed along the optical axis O, and the extended portion 62d is inserted into an outer peripheral groove 42b of the first lens frame 42 which is formed along the optical axis O. This causes the connecting terminal portion 62e to be guided to the outside of the first lens frame 42, so that the connecting terminal portion 62e can be disposed in the outer peripheral D-shaped cut portion 44a at an outer side of a front portion of the third lens frame 44. The outer peripheral groove 42b is formed offset from the inner peripheral groove 42a by an angle of about 90 degrees in the circumferential direction.

As shown in FIG. 8, the third lens frame 44 has an outer peripheral D-shaped cut portion 44b formed in the rear portion thereof, opposing to the outer peripheral D-shaped cut portion 44a in the front portion thereof. Furthermore, the third lens frame 44 has a surface wiring section 44c formed on the outer surface thereof between the front outer peripheral D-shaped cut portion 44a and the rear outer peripheral D-shaped cut portion 44b by printing. The surface wiring section 44c is provided by applying an insulative coating on the outer surface of the third lens frame 44 so as to electrically connect between the outer peripheral D-shaped cut portions 44a and 44b.

The lead electrode portion 62g provided to the connecting terminal portion 62e of the FPC connector 62 which is guided outside from the first lens frame 42 is connected to the surface wiring section 44c by soldering at the front outer peripheral D-shaped cut portion 44a of the third lens frame 44. To the rear outer peripheral D-shaped cut portion 44b, a distal end of the actuator driving cable 63 inserted through to the distal end portion 8B is provided to be connected there by soldering.

The actuator driving cable 63 has a thickness which does not exceed the outer peripheral D-shaped cut portion 44b of the third lens frame 44.

When first lens frame 42 is fitted into the third lens frame 44 to be adhesively fixed thereto, the outer peripheral groove 42b formed along the axial direction of the first lens frame 42 and the outer peripheral D-shaped cut portion 44a formed along the axial direction of the third lens frame 44 are aligned with each other to be in a predetermined phase relationship. The second lens frame 43 is fitted into the first lens frame 42 to be adhesively fixed thereto.

The above connected FPC connector 62 and the actuator driving cable 63 are sealed by an adhesive. That is, an adhesive is filled in the inner peripheral groove 42a and the outer peripheral groove 42b of the first lens frame 42, the gap between the outer surface of the second lens frame 43 and the inner periphery of the third lens frame 44, and the recess and connection of the outer peripheral U-shaped cut portion 44a of the third lens frame 44 for sealing. Further, the third lens frame 44 is covered with a heat shrinkable tube 23 at the outer periphery thereof, so as to make the connection and the portion around the filter/adjustable diaphragm unit 49 sealed in a watertight manner.

Respective operations in an observation for normal light and an NBI observation in the videoscope system of the present embodiment having the above described configuration will be explained below.

When the operation switch 9 is operated to select an observation mode for normal light, both of the filter actuator 57 and the diaphragm actuator 58 are in a non-energized state. At this point of time, the NBI filter 50 of the filter/adjustable diaphragm unit 49 is moved to a retracted position, so that the diaphragm plate 59 is at a stopped down position. Thus, a light from a subject obtained by a white light which is a normal light is formed on the CCD 22 through the diaphragm opening 59a of the diaphragm plate 59 positioned at the stopped down position, and an image pickup signal of a subject image is captured.

Figure 7A:
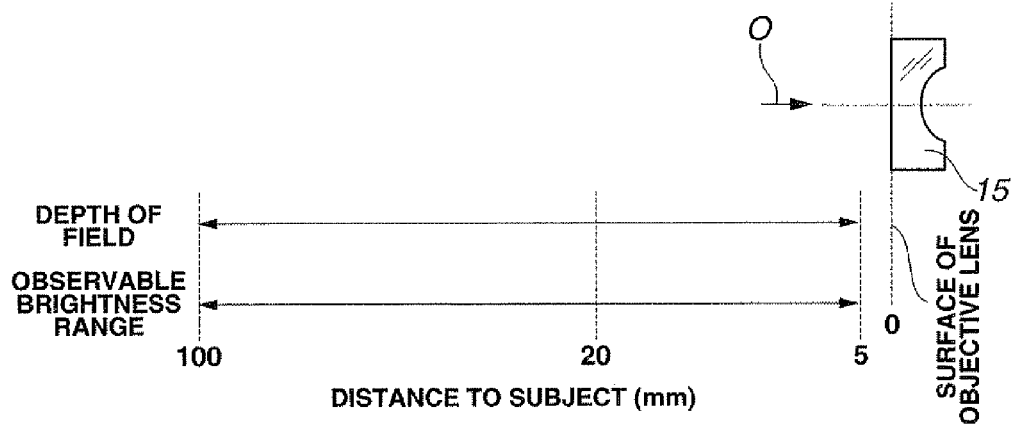
FIG. 7A is a graph illustrating the relationship between focal depth and brightness in a normal light observation with an aperture being stopped down in the videoscope system of FIG. 1.
Figure 7B:
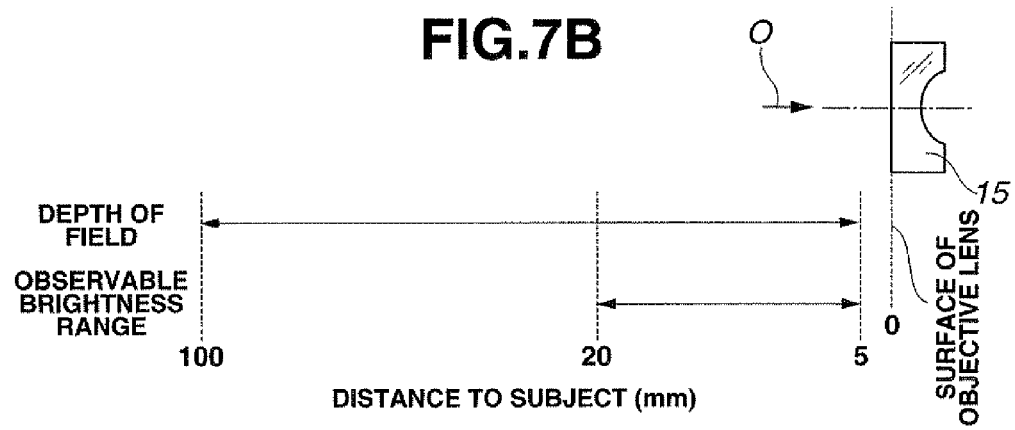
FIG. 7B is a graph illustrating the relationship between focal depth and brightness in an NBI observation with an aperture being stopped down in the videoscope system of FIG. 1.
Figure 7C:
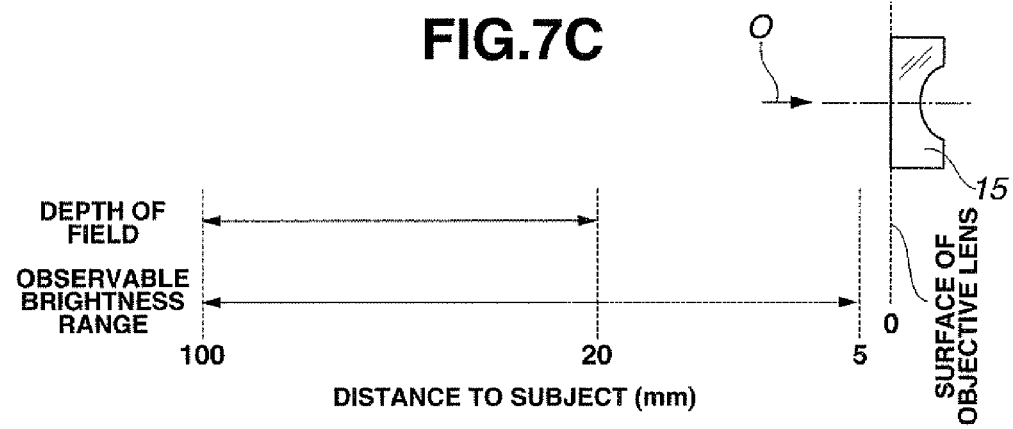
FIG. 7C is a graph illustrating the relationship between focal depth and brightness in an NBI observation with an aperture being opened up in the videoscope system of FIG. 1.

In the observation state for normal light, as shown in FIG. 7A, the depth of field is large and a sufficient brightness is obtained due to the retracted NBI filter 50, thereby the range from the far point to the near point provides a range having observable brightness. That is, the range from the far point to the near point is observable.

Meanwhile, when the operation switch 9 is operated to select a mode for NBI observation, the filter actuator 57 is switched to be in an energized state. In this state, the NBI filter 50 is positioned on the diaphragm open aperture 51a, that is, is inserted into the light path of the observation light, Thus, the mode is switched to an NBI mode in which a narrow band light from a subject through the NBI filter 50 is formed on the CCD 22, and an image pickup signal of a subject image is caught.

In a near point observation in the NBI mode, the diaphragm actuator 58 is remained in the non-energized state when the subject distance ranges from the 5 mm near point to the 20 mm middle point and a sufficient brightness is detected. That is, diaphragm plate 59 remains at the stopped down position. That is, the diaphragm is provided by the diaphragm opening 59a. In this case, as shown in FIG. 7B, the depth of field is large. And the NBI filter 50 is inserted and the diaphragm plate 59 is remained at the stopped down position, thereby the light amount is decreased. However, the observed subject distance ranges from the near point to the middle point in a near point observation state, which provides an observable depth with a sufficient brightness.

In a far point observation in the NBI mode, the diaphragm actuator 58 is switched to be in an energized state when the subject distance ranges from the 20 mm middle point to the 100 mm far point and an insufficient brightness is detected. Then, the diaphragm plate 59 is retracted to an opened-up position, as the result of that the diaphragm is provided by the diaphragm open aperture 51a. In the case, as shown in FIG. 7C, the depth of field is small. The NBI filter 50 is inserted, but light amount is increased by the opened up diaphragm, which provides a sufficient brightness to observe the subject distance from the near point to the far point. Thus, the subject distance from the middle point to the far point is secured as an observable depth.

As described above, according to the videoscope system of the present embodiment, an insertable/retractable NBI filter is not provided as a light source apparatus although the filter is applied to a dedicated video processor and an image pickup unit 41. As a result even in the videoscope system applying a normal light source apparatus, a normal light observation and an NBI observation can be performed. Moreover, as in the case of the videoscope system 100 of the first embodiment, a normal light observation can be performed in a normal manner even if a video processor which is not adapted to an observation for special light is used.

Furthermore, according to the videoscope system of the present embodiment, a reduction of the size of the videoscope in the system in which a normal light observation and an NBI observation can be performed can be achieved to the degree as that of the objective optical system having a fixed focus without an adjustable diaphragm. The system also has a good assembility, is easy to be watertight, has a good moisture resistance, and enables a check of diaphragm operation during its assembly or in a assembled unit state. The configuration of the system has less failure due to dust, or lower possibility of generation of flare, and secures the accuracy and strength of lens frames, thereby various effects can be obtained including a good optical property.

In the present embodiment also, instead of the NBI mode which is an observation mode for special light, a fluorescence mode and an observation mode for infrared light can be applied. In the case, instead of the NBI filter 50 incorporated in the filter/adjustable diaphragm unit, a fluorescence filter and a filter for infrared light observation should be applied.

Also, in addition to the NBI filter 50, when a plurality types of filters such as a filter for infrared light observation or fluorescence are incorporated into the filter/adjustable diaphragm unit, various observations for special light can be achieved in one videoscope.

In addition, when a plurality types of diaphragm plates 59 having different diaphragm openings 59a are incorporated in the filter/adjustable diaphragm unit, observations in accordance to a more number of depths can be achieved. Furthermore, diaphragm wings which are able to continuously change the inner diameter of the diaphragm opening can be used to similarly perform the observations divided at a number of depths.

Next, a videoscope system according to a third embodiment of the present invention will be explained below with reference to FIGS. 14 and 15.

A videoscope system of the present embodiment is generally similar to the videoscope system of the above second embodiment, except the configuration of an image pickup unit which is incorporated in the videoscope.

Figure 14:
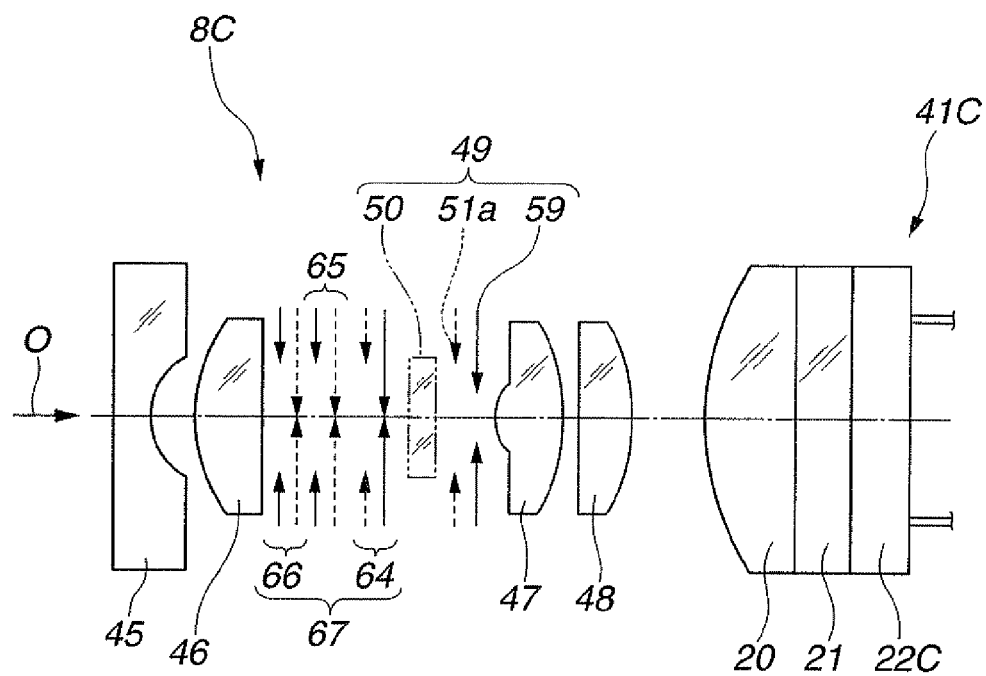
FIG. 14 is a cross sectional view showing an image pickup optical system of an image pickup unit which is incorporated in the distal end portion of a videoscope inserting section which is applied to a videoscope system according to a third embodiment of the present invention.
Figure 15:
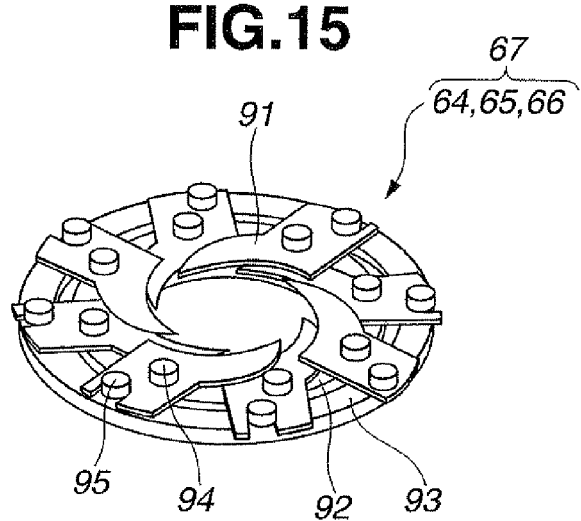
FIG. 15 is a perspective view showing an adjustable diaphragm unit which is incorporated in the image pickup unit of FIG. 14.

That is, the image pickup unit 41C of the videoscope system of the present embodiment has a CCD 22C which is the monochrome image pickup device shown in FIG. 14, an RGB filter unit 67, the image pickup optical system which is identical to that applied in the second embodiment, and the filter/diaphragm unit 49 incorporated therein. The video processor has a driving circuit for the RGB filter unit 67 and an image processing circuit of frame sequential type which is driven in synchronization with the driving circuit, incorporated therein.

The RGB filter unit 67 is a three-color filter unit which is configured with an R (red) filter unit 64, a G (green) filter unit 65, and a B (blue) filter unit 66, and is disposed in the front of the filter/diaphragm unit 49.

The filter units 64, 65, and 66 for the three colors have an identical configuration, and have filters of different colors from each other. For example, the R filter unit 64 has a pivotable ring-shaped metallic outer rotary disc 93 as shown in FIG. 15, a ring-shaped metallic inner fixing disc 92 which is fixedly disposed to the inner periphery of the outer rotary disc 93, and divided filters 91 including eight optical filter plates which transmit red color.

Each of the divided filters 91 is pivotally supported by a pivot pin 95 provided on the outer rotary disc 93 side and a supporting pin 94 provided on the inner fixing disc 9.

In the RGB filter unit 67, when the outer rotary disc 93 is driven counterclockwise for example, each of the divided filters 91 is pivoted to advance onto the observation light path to be in a completely closed state. In the closed state, the divided filters 91 function as a normal filter. To the contrary, when the outer rotary disc 93 is driven clockwise, each of the divided filters 91 is pivoted in the opposite direction to be retracted from observation light path so as to be in an opened up state.

The R filter unit 64, the G filter unit 65, and the B filter unit 66 repeatedly perform the operation to function as an RGB rotary filter. Then, image pickup signals are captured in the CCD 22C individually for RGB with the units being synchronized with each other, so that an image pickup by a frame sequential method is performed.

In a normal light observation of the videoscope system of the present embodiment, the RGB filter unit 67 is driven so that an image pickup by a frame sequential method is performed. At this time, the filter/diaphragm unit 49 causes the NBI filter 50 to be in the retracted state as in the case of the second embodiment, and the diaphragm plate 59 to be in the inserted state. Thus, a normal light observation can be performed as in the second embodiment.

Also, in an NBI observation, the RGB filter unit 67 sets the divided filters 91 to be in the retracted state. While, the filter/diaphragm unit 49 causes the NBI filter 50 to be in the inserted state as in the case of the second embodiment. In a near point observation state, the diaphragm plate 59 is in the retracted state, while in a middle to far point observation state, the diaphragm plate 59 is in the inserted state. Thus, an observation similar to the NBI observation in the second embodiment can be achieved.

According to the videoscope system of the present embodiment, a monochrome CCD can be used as the image pickup device. Since the RGB filter and the NBI filter which enable every switching can be provided in the distal end portion 8C of the videoscope, a normal light observation by the frame sequential method and an NBI observation can be performed without providing an insertable/retractable filter to the light source apparatus.

An application of the above described RGB filter unit 67 to the illumination optical system of the videoscope or to the light source apparatus provides the same effects.

Next, a videoscope system according to a fourth embodiment of the present invention will be explained below with reference to FIGS. 16 to 18.

In a videoscope system of the present embodiment, the image pickup unit disposed in the distal end portion 8D of the videoscope is not provided with an adjustable diaphragm unit, but has an adjustable diaphragm unit 78 incorporated in an illumination optical system. Other configuration of the videoscope system is similar to that of the first embodiment.

The illumination optical system disposed in the distal end portion 8D of the videoscope is configured with a light guide fiber bundle 76, an illumination lens 74, and an adjustable diaphragm unit 78. The light guide fiber bundle 76 is arranged through a light guide insertion hole 87. The illumination lens 74 is held by the lens frame 75. The adjustable diaphragm unit 78 is interposed between the light guide fiber bundle 76 and the illumination lens 74.

The distal end portion 8D has a treatment instrument insertion hole 72 formed therein on the side of the illumination optical system, so that the treatment instrument 73 is inserted through the insertion hole 72.

The distal end portion 8D also has an image pickup unit (not shown) on the side of the illumination optical system. The side portion of the distal end portion ED is covered with a distal end protecting rubber 70, and to the side portion of the distal end surface of the distal end portion SD, a distal end insulation cap 68 is attached.

The light guide fiber bundle 76 is made, after molding, by grinding the distal end surface thereof with a mouthpiece 77 being fitted to the distal end portion. The light guide fiber bundle 76 is fixedly fitted in the inner periphery of the rear portion of the lens frame 75 with the distal end surface being butted against a substrate 79 of the adjustable diaphragm unit 78 which will be explained later.

Figure 16:
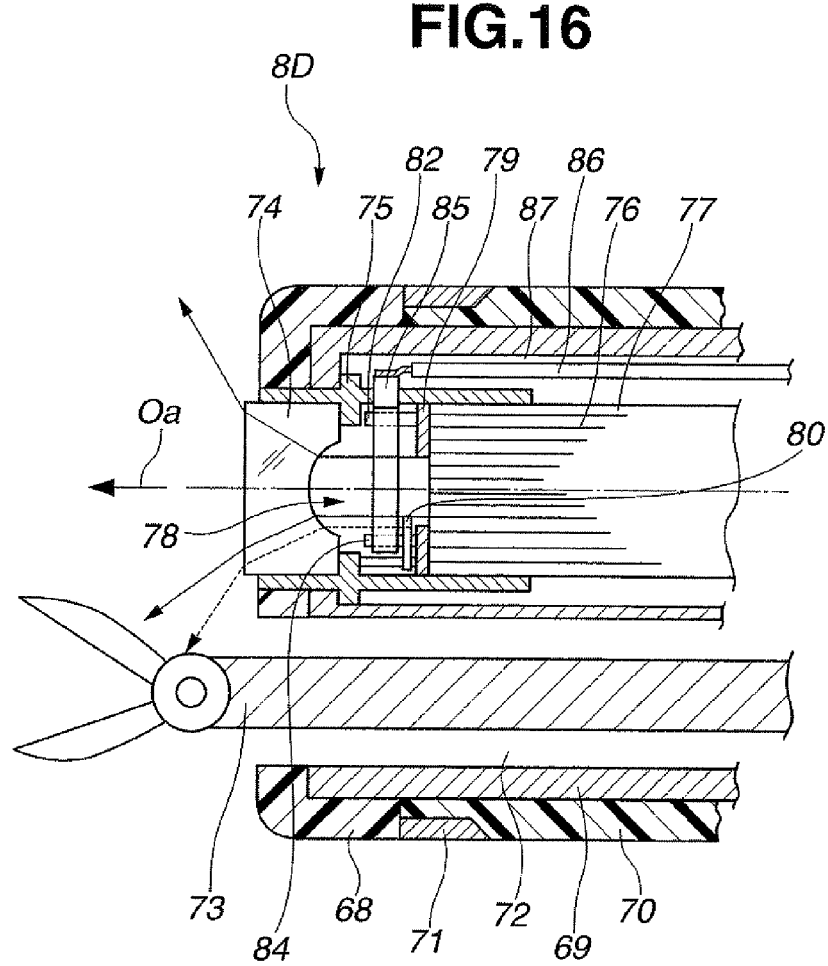
FIG. 16 is a cross sectional view showing a distal end portion of a videoscope which is applied to a videoscope system according to a fourth embodiment of the present invention, with an illumination optical system having an adjustable diaphragm unit in the distal end portion and an insertion portion of a treatment instrument.
Figure 17:
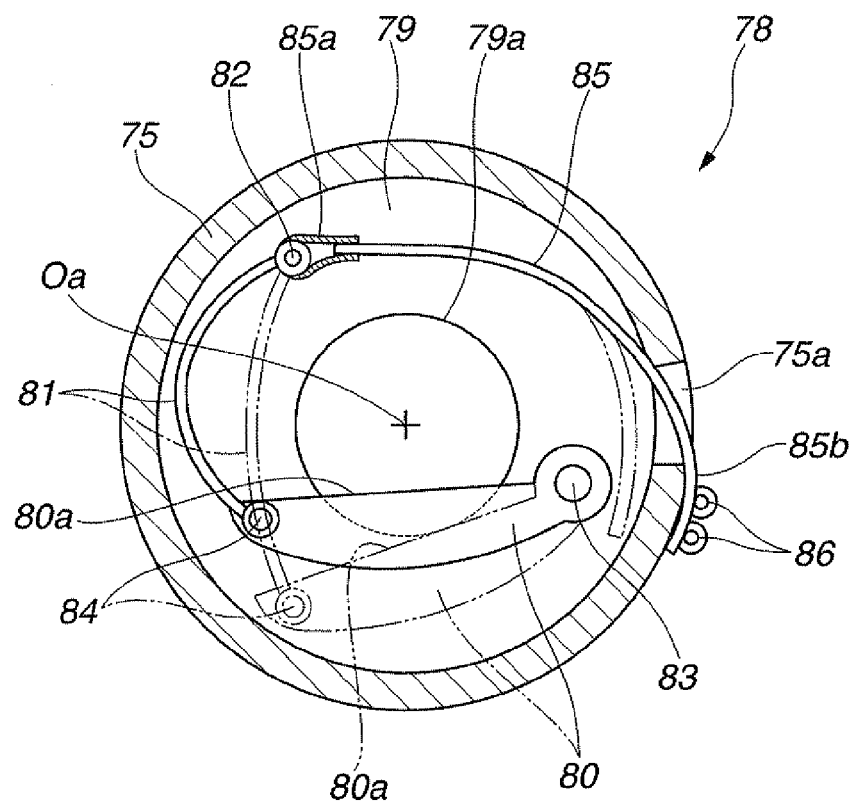
FIG. 17 is a view showing the adjustable diaphragm unit of FIG. 16, as seen from the front side thereof.
Figure 18:
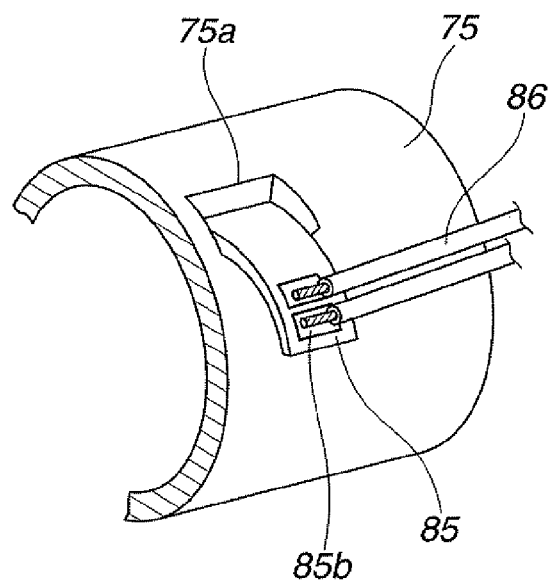
FIG. 18 is a perspective view showing a connection between an FPC connector of the adjustable diaphragm unit of FIG. 16 and an actuator cable.

The adjustable diaphragm unit 78 is, as shown in FIGS. 16 and 17, configured with a substrate 79, a diaphragm plate 80, a diaphragm actuator 81 which is an ion conductive actuator, and an FPC connector 85 which is power supplying means.

The substrate 79 is a metallic plate member having an diaphragm open aperture 79a, and is fixedly attached to the inner periphery of the lens frame 75.

The diaphragm plate 80 is pivotally supported by a supporting pin 83 provided on the substrate 79. The diaphragm plate 80 has a distal end which is coupled to the diaphragm actuator 81 via a moving pin 84.

The diaphragm actuator 81 includes an arc section, and has one end which is supported by an insulative locking pin 82 on the substrate 79 side and the other end which is coupled to the diaphragm plate 80 via a moving pin 84. Thus, as the curvature of the diaphragm actuator 81 is changed, the diaphragm plate 80 is pivotally driven around the supporting pin 83.

The diaphragm actuator 81 is driven by an actuator driving circuit 102. The diaphragm actuator 81 has a small curvature in a non-energized state in which no driving voltage is supplied, and has a large curvature in an energized state. In the energized state with a large curvature, the diaphragm plate 80 is located at the stopped down position with the edge portion 80a on the diaphragm open aperture 79a of the substrate 79 on the treatment instrument insertion hole 72 side as shown by the solid line of FIG. 17. In the non-energized state with a small curvature, the diaphragm plate 80 is located at the opened-up position where the edge portion 80a is retracted from the diaphragm open aperture 79a of the substrate 79 as shown by the chain double-dashed line.

When the diaphragm plate 80 is at a stopped down position, as shown in FIG. 16, among the illumination light emitted through the illumination lens 74, the light shown by the broken line which is irradiated to the treatment section side of the treatment instrument 73 is cut off by an edge portion 80a of the diaphragm plate 80. Thus, the light reflected by the treatment section of the treatment instrument 73 is reduced, which enables generation of flare to be suppressed without decreasing the brightness. In a case where only one illumination lens (concave lens) 74 is used, the light of the treatment section side is reduced.

The FPC connector 85 has one end having a lead electrode 85a which is connected to the portion around the locking pin 82 of the diaphragm actuator 81 by soldering. The FPC connector 85 has the other end which is, as shown in FIG. 18, guided out of the lens frame through a through hole 75a which is formed in the peripheral side portion of the lens frame 75. The other end of the FPC connector 85 has a cable connecting terminal portion 85b which is connected to an actuator connecting cable 86 by soldering.

The other end of the FPC connector 85 is adhesively fixed in a state of being guided out of the lens frame through the through hole 75a. The gap between the through hole 75a of the lens frame 75 and the FPC connector 85 is filled with an adhesive so as to maintain the inside in a watertight state.

In the videoscope system of the present embodiment having the above described configuration, as in the case of the above described first embodiment, the NBI filter 101 is retracted or inserted in the light source apparatus 3, and the diaphragm plate 80 is pivotally driven to the above described stopped down position or the opened-up position by the diaphragm actuator 81, so that a normal light observation or an NBI observation can be performed.

Especially, in the present embodiment, when the diaphragm plate 80 is disposed at the stopped down position, the light reflected by the treatment section of the treatment instrument 73 which is protruded forward from the distal end surface of the distal end portion 8D is reduced, which enables generation of flare to be effectively suppressed without decreasing the entire brightness.

Also, according to the configuration of the videoscope applied in the present embodiment, the system also has a good assembility, is easy to be watertight, has a good moisture resistance, and enables a check of diaphragm operation during its assembly or in a assembled unit state. The configuration of the system is free from failure due to dust, and secures the accuracy and strength of lens frames, thereby various effects can be obtained including a good optical property.

Next, a modified example of an adjustable diaphragm unit which is incorporated in the illumination optical system of the videoscope according to the present embodiment will be explained below with reference to FIGS. 19 and 20.

An adjustable diaphragm unit 99 of the present modified example is interposed between a light guide fiber bundle 76 and an illumination lens 88 which is a convex lens. The adjustable diaphragm unit 99 has the configuration similar to that of the adjustable diaphragm unit 24 applied in the first embodiment. That is, the adjustable diaphragm unit 99 has a diaphragm plate 97 which is pivotally supported by a supporting pin 98 provided to a substrate 96. The diaphragm plate 97 is pivotally driven by the diaphragm actuator via a moving pin 97b from the stopped down position shown in FIG. 19 to the retracted position where the diaphragm plate 97 is retracted from an diaphragm open aperture 96a of the substrate 96.

Figure 19:
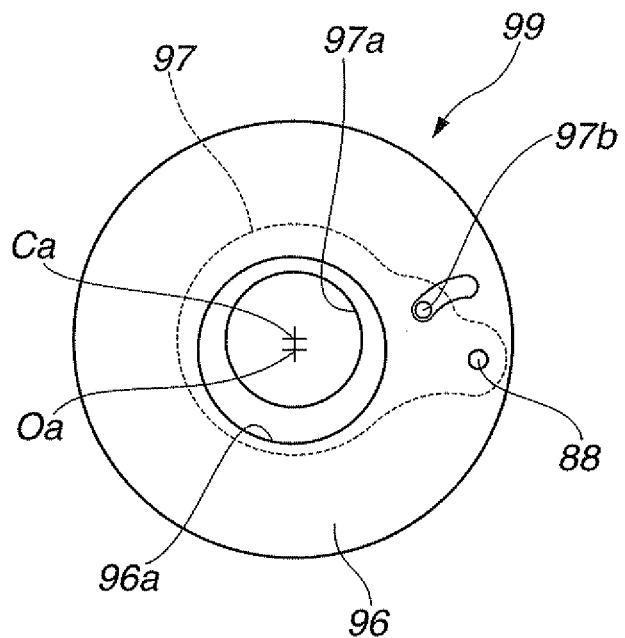
FIG. 19 is a view showing a modified example of an adjustable diaphragm unit in a stopped down state incorporated in the illumination optical system in the videoscope of FIG. 16, as seen from the front side thereof.
Figure 20:
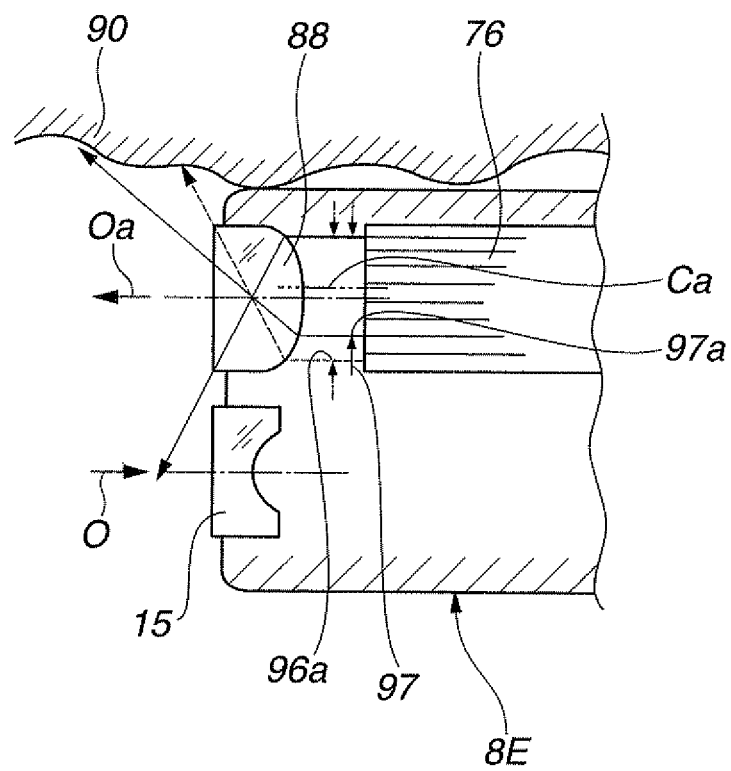
FIG. 20 is a view showing a subject irradiated by the illumination optical system of FIG. 19.

However, in the present embodiment, as shown in FIG. 19, when the diaphragm plate 97 is at the stopped down position, the diaphragm opening 97a has its central point at an eccentric position Ca which is eccentric relative to the diaphragm open aperture 96a of the substrate 96 around an optical axis for irradiation Oa. The eccentric position Ca is, as shown in FIG. 20, located at a position closer to the body wall 90 in an outward direction of the illumination optical system.

At a distal end portion of a conventional videoscope, since the illumination lens 88 is located near an outer peripheral of an insertion sections and is close to a body wall 90 to be observed, a light irradiation to the side of the distal end toward the body wall 90 is strong, and the reflected light tends to cause flare.

However, according to the adjustable diaphragm unit 99 of the present modified example, since the center of the diaphragm opening 97a of the diaphragm plate 97 which is in a stopped down state is outwardly eccentric, a light irradiation to the side of the distal end toward the body wall 90 shown by the broken line is suppressed, so that generation of flare can be suppressed.

The present invention is not limited to the above described embodiments, and various modifications can be added within a scope of not departing from gist of the invention.

What is claimed is:

1. An endoscope system including a light source apparatus and an endoscope having an illumination optical system and an objective optical system, comprising:

an operation switch for switching between a normal light observation mode using normal light and a special light observation mode using special light;

a filter for the special light observation mode which is insertable into and retractable from one of a light path of the light source apparatus, a light path of the illumination optical system of the endoscope, and a light path of the objective optical system of the endoscope, as a first light path, wherein when the special light observation mode is selected through operation of the operation switch, the filter is inserted into the first light path;

an adjustable diaphragm provided in the objective optical system of the endoscope, the adjustable diaphragm being insertable into and retractable from the light path as the first light path and a second light path, of the objective optical system of the endoscope, the adjustable diagram closing the second light path in an insertion state;

a diaphragm actuator causing the adjustable diaphragm to be insertable or retractable from the second light path to switch the second light path into a state where the diaphragm of the second light path is closed or open;

a control circuit comprising a brightness level detecting circuit to measure brightness of a subject in a state where the special light observation mode is selected through the operation of the operation switch and a filter for the special light observation is inserted into the first light path, and detecting whether the brightness is equal to or larger than a predetermined level and an actuator driving circuit that controls the diaphragm actuator according to a signal outputted from the brightness level detecting circuit and causes the adjustable diaphragm to be inserted into or retractable from the second light path; and a switch circuit for switching between driving and non-driving of the control circuit based on the operation switch and driving the control circuit when the special light observation mode is selected through the operation of the operation switch.

2. The endoscope system according to claim 1, wherein in a driving state of the control circuit, the control circuit drives and inserts the adjustable diaphragm into the second light path as a near point observation in the special light observation mode when the brightness is equal to or larger than the predetermined level, and the control circuit removes the adjustable diaphragm from the second light path as a far point observation in the special light observation mode when the brightness is below the predetermined level.

3. The endoscope system according to claim 2, wherein a diaphragm diameter in the near point observation is set to be the same as that in the case where the filter for the observation for special light is not inserted into the light path.

4. The endoscope system according to claim 1, wherein when the diaphragm actuator is in a non-conductive state, the diaphragm actuator positions the adjustable diaphragm in the second light path, and when the diaphragm actuator is in a conductive state, the diaphragm actuator removes the adjustable diaphragm from the second light path.

5. The endoscope system according to claim 1, wherein the diameter of the diaphragm opening is set to be the diffraction limit inner diameter.

6. The endoscope system according to claim 1, wherein the observation for special light is an observation using a narrow band light or an observation using fluorescence.

7. The endoscope system according to claim 1, wherein the insertable/retractable filter for the observation for special light is provided to a diaphragm of the adjustable diaphragm.

8. The endoscope system according to claim 1, wherein the endoscope further comprises:

a first substrate and a second substrate provided in the objective optical system, the first and second substrates including a diaphragm open aperture of a same diameter at a center with the diaphragm of the second light path; and a pivotally supporting pin supported by the first substrate and the second substrate, the pivotally supporting pin pivotally supporting the adjustable diaphragm so as to be insertable into and retractable from the second light path.

* * * * *